United States Patent [19]

Dallas, Jr.

[11] Patent Number: 4,812,746

[45] Date of Patent: Mar. 14, 1989

[54] METHOD OF USING A WAVEFORM TO SOUND PATTERN CONVERTER

[75] Inventor: Stanley A. Dallas, Jr., Portland, Oreg.

[73] Assignee: Thales Resources, Inc., Hillsboro, Oreg.

[21] Appl. No.: 928,593

[22] Filed: Nov. 10, 1986

Related U.S. Application Data

[63] Continuation of Ser. No. 565,171, Dec. 23, 1983, abandoned.

[51] Int. Cl.$^4$ ............................................. G01R 13/34
[52] U.S. Cl. ............................. 324/121 R; 324/99 D; 324/111; 340/384 E; 340/825.19; 340/870.2; 434/116
[58] Field of Search ............... 324/73 R, 99 D, 121 R, 324/111; 340/825.19, 870.21, 870.26, 384 E; 358/94; 375/48; 434/116; 128/701, 732, 905

[56] References Cited

U.S. PATENT DOCUMENTS

| | | | |
|---|---|---|---|
| 3,007,259 | 11/1961 | Abma et al. | 434/116 |
| 3,081,431 | 3/1963 | Werner et al. | 324/99 D |
| 3,721,969 | 3/1973 | Stewart, Jr. | 340/870.26 X |
| 3,800,082 | 3/1974 | Fish | 358/94 |
| 3,828,252 | 8/1974 | Wolff | 324/99 D |
| 3,869,667 | 3/1975 | Cannicatti | 324/102 X |
| 3,907,434 | 9/1975 | Coles | 356/152 |
| 4,000,565 | 1/1977 | Overby et al. | 434/116 |
| 4,105,966 | 8/1978 | Lennon et al. | 324/102 X |
| 4,112,425 | 9/1978 | Zobrist et al. | 179/2 DP X |
| 4,155,037 | 5/1979 | Mazur | 324/111 |
| 4,238,783 | 12/1980 | Miller | 340/870.26 |
| 4,485,400 | 11/1984 | Lemelson et al. | 179/2 DP X |
| 4,576,178 | 3/1986 | Johnson | 128/670 |
| 4,625,732 | 12/1986 | Kása et al. | 128/670 |

OTHER PUBLICATIONS

Horowitz et al., *The Art of Electronics*, Cambridge Univ. Press, 1980.
Rev. Sci. Instrum., vol. 51, No. 12, Salt et al., "General Purpose Talking Laboratory Instrument for the Visually Handicapped", Dec. 1980, pp. 1710-1713.
Mukhopadhyay, A., "Measurements of Lightning Induced Arrester Ground Current . . . ", Electric Power Systems Research, vol. 2, No. 4, Dec. 1979, pp. 279-291.
Ward, R., "Build This $60 Modem", Radio-Electronics, vol. 52, No. 6, Jun. 1981, pp. 39-42, 70.
Wagner, W., "Digial Voltmeter has Audible Output", Electronics, vol. 52, No. 7, Mar. 29, 1979, pp. 120-122.
Fowler, T., "Digital Meter for the Blind", Wireless World, vol. 80, No. 1464, Aug. 1974, pp. 283-286.

*Primary Examiner*—Jerry Smith
*Assistant Examiner*—Stephen M. Baker
*Attorney, Agent, or Firm*—Foley & Lardner, Schwartz, Jeffery, Schwaab, Mack, Blumenthal & Evans

[57] ABSTRACT

A method of using a waveform to sound pattern converter that produces an audible image of a time dependent signal by digitizing the signal to produce a plurality of discrete level signals, and produces a different audible tone signal for each level of the discrete level signals. A speaker is provided for producing audible sounds and circuitry is provided for driving the speaker to produce an audibly perceptible reference frame indicative of a predetermined time duration and also for driving the speaker with the audible tone signals such that the audible tone signals have the same time orientation with respect to each other as the discrete level signals have in the time dependent signal. The sounds are provided to listener to enable the listener to distinguish the shape of the time dependent signal based on the position and time relation of the tone signals relative to the reference time frame signal.

11 Claims, 2 Drawing Sheets

METHOD OF USING A WAVEFORM TO SOUND PATTERN CONVERTER

This application is a continuation of application Ser. No. 565,171, filed Dec. 23, 1983 now abandoned.

BACKGROUND OF THE INVENTION

1. Field of the Invention

This invention relates to systems for converting electrical signals into sound patterns and more particularly to systems which can convert the visual readout of an instrument such as an oscilloscope into a sound pattern representative of the visual readout.

2. Discussion of Related Art

The vast majority of instruments used for measuring and testing applications use visual readouts to indicate the quantity being measured. Such instruments, such as an oscilloscope, are invaluable in certain fields of endeavor. However, these instruments have certain drawbacks. First, it is necessary that a user focus his or her attention on the visual readout in order to be constantly aware of the status of the measured quantity. Therefore, if the user wishes to make adjustments to a system containing the measured parameter, he or she must either make the adjustments without keeping careful track of the effect of the adjustment as indicated on the visual readout, or must constantly watch the readout and make the adjustments only by physically feeling the elements being adjusted.

Furthermore, these instruments cannot be used by persons handicapped by limited sight. If such a person is to use, for example, an oscilloscope, he or she must have someone else provide an aural description of the status of the visual readout.

Consequently, it would be useful to have a system which can directly produce an audible representation of a measured parameter in order to replace or augment a measuring instrument such as an oscilloscope. Such an instrument could produce a sound pattern representative of the visual pattern of an ordinary oscilloscope or other measuring and testing instrumentation.

Systems are already known for producing sound pattern representations of certain quantities. For example, U.S. Pat. No. 3,007,259 to Abma et al shows an optophone which comprises an optical head that can be passed over printed material. The system produces a unique sound pattern for each letter of the alphabet to enable a sightless person to read the printed material aurally.

U.S. Pat. No. 3,800,082 to Fish discloses a system for producing sound patterns representing various objects wherein the raster scan display of an oscilloscope CRT is detected by a photomultiplier tube. The object to be represented is placed between the CRT and photomultiplier tube. The signal from the multiplier tube causes a sound to be generated representing the position of the illuminated portion of the oscilloscope CRT which is not covered by the object.

U.S. Pat. No. 3,907,434 to Coles discloses a binaural sight system in which two cameras are used which generate image signals representative of optical images projected thereonto. The cameras are positioned in horizontally spaced relation and are independently connected to right and left earphones. The cameras are scanned in opposite directions and the output from the cameras are used to drive the earphones U.S. Pat. No. 4,000,565 to Overbee et al discloses an apparatus for converting silent digital visual display characters into sequentially enunciated audible tones which blind or visually handicapped persons can recognize.

SUMMARY OF THE INVENTION

One object of the present invention is to provide a system which can transform electrical waveform signals into sound pattern configurations representative of the signals.

Another object of the present invention is to provide a waveform to sound pattern converter which can be used with an existing oscilloscope to produce an audible representation of the pattern displayed on the oscilloscope CRT.

A further object of the present invention is to provide a waveform to sound pattern converter which can be used to augment an oscilloscope or other measuring device to allow field service personnel to devote their attention to manipulating the electrical probes or the like connected to the oscilloscope and still be able to determine when a desired electrical signal exists by hearing a sound pattern representing the signal.

Another object of the present invention is to provide a system which will enable a visually handicapped person to determine an electrical waveform by listening to its sound pattern.

Yet another object of the present invention is to provide a waveform to sound pattern converter which is relatively simple to use and uncomplicated in structure.

In accordance with the above and other objects, the system of the present invention produces an audible image of a time dependent signal. The system comprises circuitry for digitizing the signal to produce a plurality of discrete level signals representative of the signal, circuitry for producing a different audible tone signal for each level of the discrete level signals, a speaker for producing audible sounds, and driving circuitry for the speakers to produce an audibly perceptible reference frame indicative of a predetermined time duration and for driving the speaker with the audible tone signals such that the audible tone signals have the same time orientation within the reference frame with respect to each other as the discrete level signals have in the time dependent signal.

The discrete level signals can be in the form of voltage signals and the circuitry for producing different audible tone signals can be a voltage to frequency converter in the form of a voltage controlled oscillator.

In accordance with other aspects of the invention, the perceptible reference frame is a time reference frame and the speaker driving circuitry includes a reference generator for producing an audible reference signal having a period equal to the period of the time reference frame.

The system can also include a sampling circuit for sampling the time dependent signal to produce a sampled lower frequency signal in the audible range when the time dependent signal has a frequency greater than the highest audible frequency.

The sampling circuit can include a memory having a plurality of locations and circuitry for writing the discrete level signals into the memory locations at a first speed and reading information out of the memory locations at a second speed. The memory can comprise two memory units wherein information is written into one of the memory units at one of the speeds and simultaneously information is read out of the other memory unit at the other speed.

The digitizing circuit can include both an analog to digital converter and a digital to analog converter connected to a memory, and circuitry for writing information into the memory at high speed (from the analog to digital converter) and reading the information out of the memory at low speed to the digital to analog converter.

BRIEF DESCRIPTION OF THE DRAWINGS

The above and other objects of the present invention will become more readily apparent as the invention is more clearly understood in connection with the following detailed description of the preferred embodiments, reference being had to the accompanying drawings in which like reference numerals represent like parts throughout and wherein.

DETAILED DESCRIPTION OF THE PREFERRED EMBODIMENTS

Figure 1:
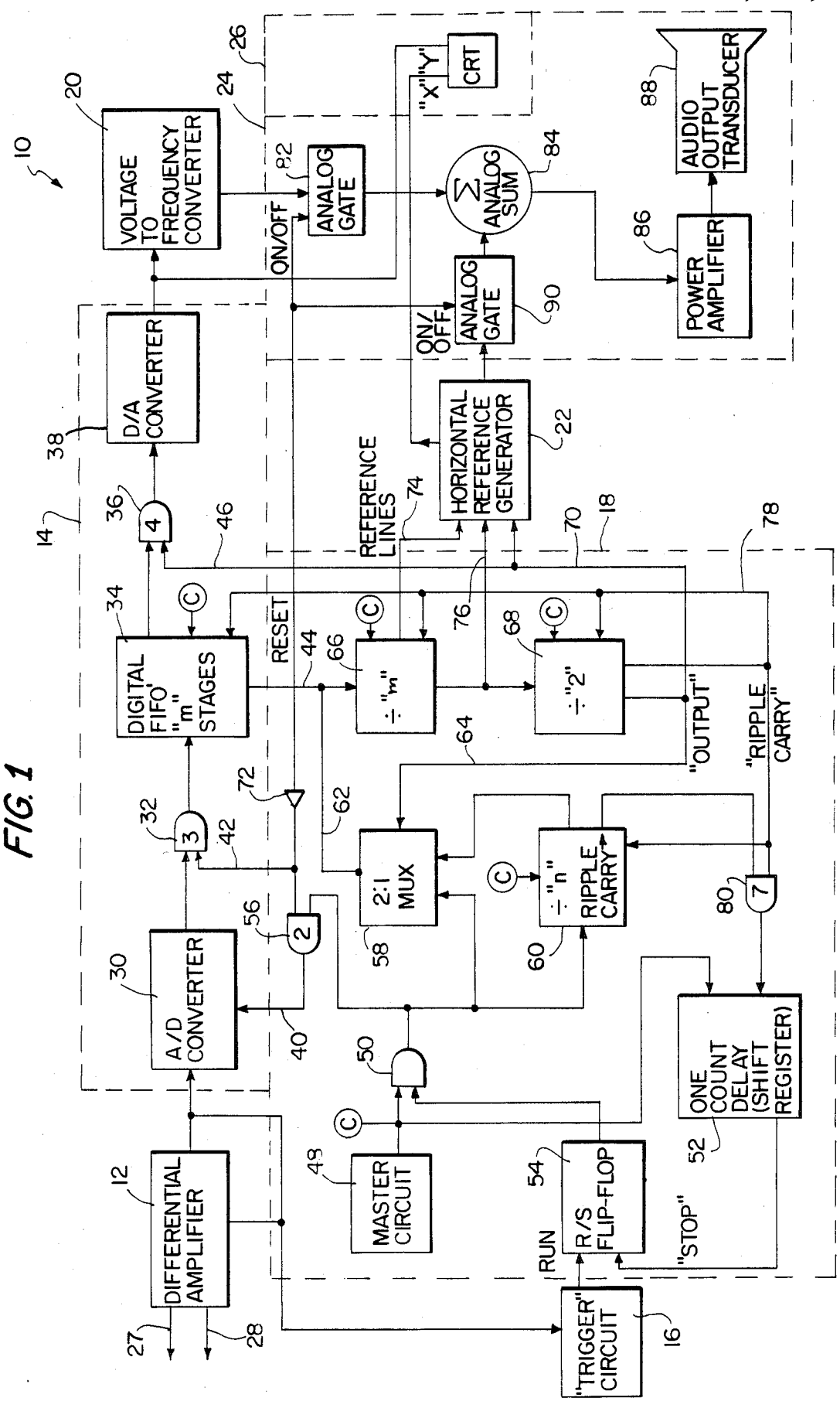
FIG. 1 sets forth a block diagram of the waveform to sound pattern converter of the present invention.

As shown in FIG. 1 of the drawings, the waveform to sound pattern converter 10 comprises a differential amplifier 12 connected to a high speed in, low speed out memory 14 which operates in accordance with a trigger circuit 16 and a synchronization and timing circuit 18 to store data related to a signal received by differential amplifier 12 and read the data out at a low speed to voltage to frequency converter 20. A horizontal reference circuit 22 is connected to receive timing signals from synchronization and timing circuit 18 and output a horizontal reference frequency. The signals from the horizontal reference circuit 22 and voltage to frequency converter 20 are received by audio output circuit 24 and converted to an audible signal. The output of memory circuit 14 can also be passed to cathode ray tube display 26 together with the horizontal reference output of circuit 22 to provide a visual display corresponding to the audio signal output from circuit 24.

Differential amplifier 12 has input lines 27 and 28 which may be, for example, connected to high and low voltage electrical probes, respectively. Differential amplifier 12 produces an output which is free of common mode noise and is indicative of the amplitude of the signal received on lines 27 and 28. The present invention is designed to provide an audio output which is representative of the display on an oscilloscope. Accordingly, differential amplifier 12 and leads 27 and 28 can be components of an oscilloscope. In order to construct the present invention, all that need be done is that a lead be connected to the output of the oscilloscope differential amplifier.

Trigger circuit 16 can be a conventional trigger circuit found in an oscilloscope. The purpose of trigger circuit 16 is to begin each sweep of the oscilloscope display at the same point on a repetitive input signal. Trigger circuit 16 performs essentially the same function in the waveform to sound pattern converter of the present invention and, accordingly, an oscilloscope trigger circuit can be used by simply connecting a lead to the trigger circuit output.

Any high frequency input signal detected by differential amplifier 12 must be essentially slowed down in time in order for the waveform to sound pattern converter of the present invention to produce an audible representation of the signal. For this purpose, memory 14 is provided. Memory 14 receives the signal from differential amplifier 12 and essentially samples the signal by selecting and digitizing a predetermined proportion of signal frames and converting the digitized signal frames into analog signals. These analog signals are used to drive voltage to frequency converter 20 which can be a voltage controlled oscillator. Voltage to frequency converter 20 is set up such that the larger magnitude analog signals received produce high frequency output signals and the lower magnitude analog signals produce relatively lower frequency output signals. Accordingly, memory 14 slows down the input signal received from differential amplifier 12 and voltage to frequency converter 20 produces an output signal the frequency of which increases as the amplitude of the slowed input signal becomes more positive and decreases as the amplitude of the slowed input signal becomes more negative.

Horizontal reference circuit 22 receives timing signals from synchronization and timing circuit 18 indicating the beginning of each new frame of information transmitted from voltage to frequency converter 20 to audio output circuit 24. Horizontal reference circuit 22 produces an audio frequency signal indicative of each new frame of information. This signal can take the form of a single burst, a variable frequency tone, a series of tones, or the like. The period of this signal is equivalent to the period of the information frame which it signifies. This reference signal is added to the signal from voltage to frequency converter 20 in audio output circuit 24. The resultant signal is an audible reference signal indicating the duration of each frame of information together with a varying frequency signal indicative of the shape of the signal received by differential amplifier 12. This varying frequency signal increases and decreases in frequency to indicate more positive and less positive (or negative) amplitudes, respectively, of the signal input to differential amplifier 12. The relationship of each specific frequency of the varying frequency signal to the reference signal is the same as the relationship of the corresponding amplitude portion of the input signal to the display of an oscilloscope when viewed on the oscilloscope Memory 14 comprises a high speed analog to digital (A/D) converter 30 which is connected to receive the output of differential amplifier 12. A/D converter is connected through AND gate 32 to a digital first-in first-out (FIFO) memory 34. The output of memory 34 is passed through AND gate 36 to a digital to analog (D/A) converter 38, the output of which is connected to voltage to frequency converter 20. Operation of A/D converter 30 is controlled by synchronization and timing circuit 18 through line 40. Gate 32 is enabled or disabled by a signal sent from circuit 18 on line 42. Also, sequencing of FIFO memory 34 is effected by circuit 18 through a signal on line 44. In order to enter information into FIFO memory 34, converter 30 is enabled m times at a high rate of speed and m outputs are passed through gate 32 and written into the m stages of FIFO memory 34 at high speed. Converter 30 and gate 32 are then disabled and gate 36 is enabled by a signal on line 46. Low speed pulses are then applied through line 44 to FIFO memory 34 until all m stages of memory 34 have been read out into D/A converter 38 which outputs an analog signal to voltage to frequency converter 20.

Synchronization and timing circuit 18 contains a master clock 48 which is connected to one input of AND gate 50, to all the counters (DIVIDER circuits), and to the clock input of one stage shift register 52. The second input of AND gate 50 is connected from the non-inverted output of flip flop 54 which receives inputs from trigger circuit 16 and shift register 52. The output of AND gate 50 is connected to one input of an AND gate 56, one input of a multiplexer 58, and to the input of a programmable divide by n circuit 60. The output of divider circuit 60 is passed to a second input of multiplexer 58. The input of multiplexer 58 from AND gate 50 comprises a high speed input and the input from circuit 60 comprises a low speed input. Multiplexer 58 connects either the high or low speed inputs to output line 62 depending on the status of a select input which is connected to line 64. Output line 62 is connected to input line 44 of memory 34 and is also connected to the input of divide by m counter 66. The output of counter 66 is connected to the input of divide-by two counter 68, the output of which is connected to line 64 which, as discussed above, activates the select input of multiplexer 58. The output of divider 68 is also connected through line 70 to the input of horizontal reference generator 22, line 46 which, as discussed above, is one input to AND gate 36, audio output circuitry 24, and through inverter 72, to line 42 and to an input of AND gate 56 and an input of gate 32. Divider 66 has a set of outputs which are connected through line 74 to horizontal reference generator 22. Also, the output of divider 66 is connected through line 76 to horizontal reference generator 22. Divider 68 also has a ripple carry output which is connected through line 78 to the reset inputs of divider 60, divider 66, divider 68, and FIFO memory 34 as well as to one input of an AND gate 80. Programmable divider 60 also has a ripple carry output connected to an input of AND gate 80. The output of AND gate 80 is connected to the data input of shift register 52.

Audio output circuitry 24 includes an analog gate 82 which receives the output of voltage to frequency converter 20 and also receives an output on line 70 from divider 68. The output of analog gate 82 is connected to an analog summing circuit 84 which drives power amplifier 86 connected to audio output transducer 88. A second analog gate 90 receives the output of horizontal reference generator 22 and also receives an output on line 70 from divide by two circuit 68. The output of analog gate 90 is also passed to summing circuit 84 where it is added to the output of analog gate 82.

In operation, trigger circuit 16 begins the data conversion cycle by setting R/S flip flop 54 when it senses a predetermined position on the input signal. The output of flip flop 54 enables AND gate 50 so as to pass clock pulses from master clock 48 to AND gate 56. As long as divide by two counter 68 passes a low output through line 70, this low output is inverted to a high input in inverter 72 and enables AND gate 56 and AND gate 32. Accordingly, clock pulses from master clock 48 trigger A/D conversions in converter 30 and these conversions are passed through AND gate 32 to digital FIFO memory 34. Line 70 is also connected to input line 46 of AND gate 36. Accordingly, the low signal on line 70 inhibits AND gate 36 thus blocking the digital FIFO signals from memory 34 from being passed to D/A converter 38. At the same time, analog gates 82 and 90 are in the blocking state thus preventing any signals from reaching analog summer 84.

Converted signals from converter 30 are passed to memory 34 and fill up the m stages of that memory. This operation is carried out at high speed due to the fact that the output of counter 68 is passed through line 64 to the select input of multiplexer 58. A low signal on line 64 causes multiplexer 58 to select the high speed output from AND gate 50 and pass this output to FIFO memory 34. Accordingly, the writing process in FIFO memory 34 is synchronized with the conversion process in converter 30 which processes are carried out at the rate of master clock 48. One count after the m stages of memory 34 are full, counter 68, which receives the high speed clock pulses divided by m from counter 66, produces a high output on lines 64 and 70. This causes multiplexer 58 to switch to the low frequency input from programmable divider 60. Divider 60 can be selected to produce any desirable low speed output signal. Alternatively, a separate clock could be used in place of divider 60, if properly synchronized. The low speed clock pulses from multiplexer 58 are used to read out the data which has been stored in digital FIFO 34. The low speed is used to slow down the signal to rates that can be followed by the human ear. At the same time, gates 32 and 56 are blocked by the inverted signal on line 70 from inverter 72 and gate 36 is enabled to pass the data read out from memory 34 to D/A converter 38. The D/A converter 38 translates the digitized voltage levels back to analog voltage levels which are now greatly stretched out in time. The analog output of D/A converter 38 causes the voltage to frequency converter 20 to translate the slowed signal voltage to a data frequency. It should be noted in this regard that the input signal to differential amplifier 12 has not only been slowed down in time, but the electrical signals amplitude has now been converted to an audio frequency. This frequency is directly proportional to the amplitude and polarity of the electrical signal and is passed through analog gate 82 to summer 84. The horizontal reference signal from generator 22 is passed through analog gate 90, which is also enabled at this time, to summer 84. Horizontal reference generator 22 produces an audio signal indicative of each frame of information which is passed to the analog summer 84 from gate 82. Generator 22 can operate in various ways. The simplest form of a generator would be one which produces a low frequency reference signal for one-half of each information frame as defined by the output of counter 66 so that a user of the device will be easily able to recognize the first half of a frame versus the second half of a frame. Alternately, the reference sound can take the form of a signal which changes for each predetermined portion of a reference frame to divide the frame into quarters, eighths, etc. Accordingly, analog summer produces an output signal to power amplifier 86 which is the summation of the data signal from voltage to frequency converter 20 and the reference signal from generator 22. This signal is amplified and output through transducer 88 which may be a conventional audio speaker.

When the last byte of stored data is being read out of digital FIFO 34, the ripple carry of divide by two counter 68 sends a reset signal to its own reset input, the reset input of counter 60 and the reset input of counter 66 as well as to the reset input of FIFO memory 34. This signal is also sent to AND gate 80 which receives a coincident ripple carry signal from counter 60. On the next count, the output of counter 68 goes low and all counters are reset to zero. At the same time, shift register 52 resets flip flop 54 and holds it in the reset mode for one clock pulse from clock 48. Now the entire system has been reset to the initial position and is ready to take additional data. The system then waits for the next trigger signal from trigger circuit 16 to start the next cycle.

The system described above contains only a single signal converter and translator. By adding a second such system, together with the proper synchronization circuitry, it is possible to obtain a continuous audio output.

Figure 2:
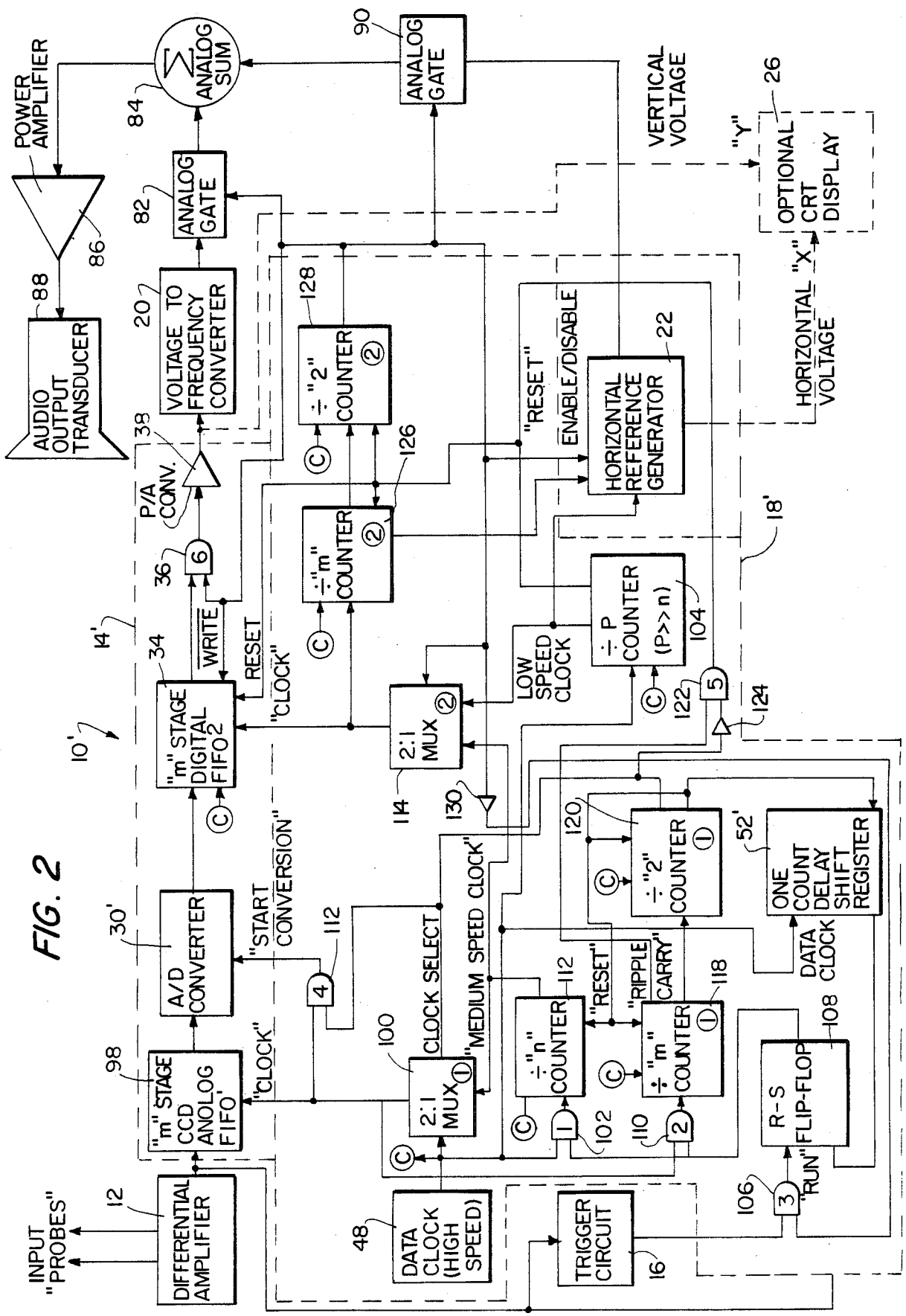
FIG. 2 sets forth a block diagram of a second embodiment of the waveform to sound pattern converter of the present invention.

The embodiment of FIG. 1 has a disadvantage in that A/D converter 30 must be capable of performing conversions at high speed. Such converters are available but are usually expensive. Accordingly, it would be preferable to be able to use lower cost A/D converters and obtain the same result. FIG. 2 shows a circuit 10' which is designed to do just that.

In circuit 10', components similar to those of circuit 10 are labeled with similar reference numerals. As with circuit 10, a differential amplifier 12 produces an output signal which is received by trigger circuit 16 and is received by a high speed in, low speed out, memory circuit 14'. Memory circuit 14' is connected to: voltage to frequency converter 20 which passes a frequency converted signal through analog gate 82 to analog summer 84. Operation of memory 14' is under the control of synchronization and timing circuit 18' which also controls horizontal reference generator 22. The output of reference generator 22 is gated through analog gate 90 to analog summer 84 where it is added to the output of gate 82.

The difference between memory circuit 14' of circuit 10' and memory circuit 14 of circuit 10 is that memory circuit 14' includes an m stage charge couple device (used as an analog FIFO memory) 98 before A/D converter 30'. FIFO 98 serves to slow down the analog signal from amplifier 12 so that converter 30' can be a low speed, relatively inexpensive, converter.

In order to utilize FIFO memory 98, synchronization and timing circuit 18' is substantially more complex than circuit 18 of circuit 10.

Circuit 18' includes a high speed data clock 48 which is connected to a first multiplexer 100 as one input to the multiplexer. The data clock output is also connected to one input of AND gate 102 and to a divide by p counter 104. Trigger circuit 16 is connected through AND gate 106 to the set input of flip flop 108. The output of flip flop 108 is connected to AND gate 110 as well as to the second input of AND gate 102. The output of AND gate 102 is connected to the input of divide by n counter 112. The output of counter 112 is connected as a medium speed clock input to multiplexer 100 and to a second multiplexer 114. The output of multiplexer 100 is connected to the clock input of FIFO 98, to the second input of AND gate 116, and to the second input of AND gate 110. The output of AND gate 110 is connected to the input of divide by m counter 118. Counter 118 has an output connected to divide by two counter 120 and also has a ripple carry output connected as one input to AND gate 122. Counter 120 has an output connected through inverter 124 to the second input of AND gate 122, and as the clock select input of multiplexer 100 as well as the second input to AND gate 116. Counter 120 also has a ripple carry output which is connected to the reset inputs of counters 112, 118 and 120 as well as to the data input of a one count shift register 52'. The clock input of shift register 52' is connected to the output of data clock 48. The output of shift register 52' is connected to the reset input of flip flop 108.

The output of AND gate 116 is connected to the enable input of converter 30'. AND gate 116 serves to pass clock pulses from multiplexer 100 to converter 30' in synchronism with the clock pulses applied to FIFO 98 when the output of counter 120 is high.

The output of AND gate 122 is connected to the reset inputs of divide by p counter 104, divide by m counter 126, and divide by 2 counter 128 as well as the reset input of m stage digital FIFO memory 34.

As discussed above, counter 104 receives its input from data clock 48. The output of counter 104 acts as the low speed clock input to multiplexer 114 and is also passed to horizontal reference generator 22. The output of multiplexer 114 is connected to the clock input of FIFO memory 34 as well as the input of divide by m counter 126. The output of counter 126 is passed to divide by 2 counter 128, the output of which is connected to the write input of FIFO memory 34, AND gate 36, analog gate 82, analog gate 90, horizontal reference generator 22, the clock select input of multiplexer 114, and, through inverter 130 to AND gate 106. Counter 126 also has reference lines output which are connected to horizontal reference generator 22 through line 132.

In operation, the amplified signal from differential amplifier 12 is received by m stage CCD analog FIFO memory 98 and trigger circuit 16. As soon as the trigger circuit activates flip flop 108, divide by m counter 118 starts counting clock pulses as the analog signals enter FIFO 98 A/D converter 30' is not processing data during this portion of the cycle. When divide by m counter 118 is full, its ripple carry output passes through AND gate 122 (since the output of inverter 124 is still "HIGH") to reset m stage digital FIFO 34 as well as counters 126, 128 and 104. At this time, the CCD FIFO 98 is full of the signal to be transformed to an audio sound pattern.

The next clock pulse from clock 48 causes divide by two counter 128 to go low and divide by two counter 120 to go high. In addition, divide by m counter 118 returns to zero. This switches multiplexers 100 and 114 to the medium speed clock obtained from the divide by n counter 112. The same signal activates AND gate 116 allowing the medium speed clock to trigger A/D conversions once for each medium speed clock pulse. The m stage digital FIFO 34 now reads in the digitized signal from the A/D converter 30'.

When divide by m counter 118 and divide by m counter 126 are full, all of the CCD FIFO data has been digitized and stored in m stage digital FIFO 34. At this point, the divide by two counter 120 ripple carry output goes high. The beginning of the next medium speed clock pulse causes divide by two counter 128 to go high also. This causes multiplexer 114 to select the low speed clock to drive divide by m counter 126 and digital FIFO 34. This enables AND gate 6 so that the stored data from FIFO 34 can reach the D/A converter 38. This also enables the two output analog gates 82 and 90 to open so that audio signals can reach the audio output transducer 88. At the same time, one count shift register 126 resets flip flop 108 and AND gate 106 is inhibited by the high state of divide by two counter 128.

At this point, the low speed section of the circuit transfers the data stored in m stage digital FIFO 34 to the output D/A converter 38 through AND gate 36. D/A converter 38 translates the digital data to an analog output voltage, the amplitude of which is directly proportional to the amplitude and polarity of the electrical signal that was stored in the CCD FIFO 98, and then transferred to digital FIFO 34. This analog voltage is translated, in turn, to an audio frequency by the voltage to frequency converter 20. A zero reference frequency can be used to divide the audio output into frequencies corresponding to positive and negative polarities. The frequency of the output signal above the zero reference signal is directly proportional to the amplitude of the original input signal (times its polarity) received by differential amplifier 12.

The voltage to frequency converter output in the horizontal reference output are added in the analog summer. Finally, the summed signals are amplified by the power amplifier 86 and the amplified signal is converted to an audible signal by the audio output transducer which may be a conventional loud speaker.

When the last byte of data has been read out of the digital FIFO 34, the divide by two counter 128 goes low enabling AND gate 106 again and closing the analog gates in the output section of the circuit. At this point, only the m stage CCD analog FIFO 98 and the divide by P counter 104 are functioning until the next trigger signal sets the R/S flip flop 108 into the run state.

The worst case condition which can occur during startup operation is if the divide by two counter 128 starts in the high state, flip flop 108 starts in the low state, divide by two counter 120 starts in the low state, and the divide by m counter 118 ripple carry output is high. In this condition, the divide by two counter 128 will go low on the next count and triggering will then start and operation of the circuit will continue as described above.

If divide by two counter 128 comes on high, and the circuitry is counting, divide by m counter 126 will always count until divide by two counter 128 goes low. A normal cycle will then start at this time.

As with circuit 10, circuit 10' is shown to contain only a single converter and translator. By adding a second such system, together with proper synchronization circuitry, it is possible to obtain a continuous audio output.

The foregoing description of the preferred embodiments is set forth for the purpose of illustrating the present invention but is not considered to limit the invention in any manner. Clearly, numerous additions, modifications, and other changes can be made to the present invention by one of ordinary skill in the art without departing from the scope thereof, as set forth in the appended claims.

What is claimed is:

1. A method comprising:
    digitizing a time dependent signal to produce a plurality of discrete level signals representative of said time dependent signal;
    producing a different audible tone signal for each level of said discrete level signals;
    producing audible sounds by driving a speaker to produce an audibly perceptible reference frame indicative of a frame time duration using a signal which is separate from said audible tone signals and driving said speaker with said audible tone signals such that said audible tone signals have the same time orientation with respect to each other as said discrete level signals have in said time dependent signal; and
    providing said audible sounds to a human listener to enable said listener to distinguish the shape of said time dependent signal based on the position and time relation of said audible tone signals relative to said reference frame signal.

2. The system as set forth in claim 1, wherein said discrete level signals are voltage signals and said step of producing a different audible tone signal comprises using a voltage to frequency converter.

3. The method as set forth in claim 1, wherein said digitizing step comprises using an analog to digital converter.

4. The method as set forth in claim 1, wherein said perceptible reference frame is a time reference frame, and said step of producing audible sounds includes producing an audible reference signal having a period equal to the period of said reference frame.

5. The method as set forth in claim 1, wherein said time dependent signal is a signal having a frequency above a range of audible frequencies perceptible by human beings, and further wherein said digitizing step includes sampling said time dependent signal to produce a sample signal in the audible range.

6. A method comprising:
    digitizing a time dependent signal to produce a plurality of discrete level signals representative of said time dependent signal;
    producing a different audible tone signal for each level of said discrete level signals;
    producing audible sounds by driving a speaker to produce an audibly perceptible reference frame indicative of a predetermined time duration and driving said speaker with said audible tone signals such that said audible tone signals have the same time orientation with respect to each other as said discrete level signals have in said time dependent signal; and
    providing said audible sounds to a human listener to enable said listener to distinguish the shape of said time dependent signal based on the position and time relation of said audible tone signals relative to said reference frame signal,
    wherein said digitizing step includes writing values from said time dependent signal into memory locations at a first speed and reading information out from said memory locations at a second speed.

7. A method comprising:
    digitizing a time dependent signal to produce a plurality of discrete level signals representative of said time dependent signal;
    producing a different audible tone signal for each level of said discrete level signals;
    producing audible sounds by driving a speaker to produce an audibly perceptible reference frame indicative of a frame time duration using a signal which is separate form said audible tone signals and driving said speaker with said audible tone signals such that said audible tone signals have the same time orientation with respect to each other as said discrete level signals have in said time dependent signal;
    providing said audible sounds to a human listener to enable said listener to distinguish the shape of said time dependent signal based on the position and time relation of said audible tone signals relative to said reference frame signal;
    wherein said time dependent signal is a signal having a frequency higher than the highest audible frequency, and further wherein said digitizing step includes sampling the time dependent signal to produce a sample signal in the audible range, and wherein said sampling step includes writing said discrete level signals into memory locations at a first speed, and reading said information out of said locations at a second speed.

8. The method as set forth in claim 7, wherein said memory comprises two memory units and said sampling step comprises writing information into the locations of one of said memory units and simultaneously reading information out of the memory locations of the other of said memory units.

9. A method comprising:
digitizing a time dependent signal to produce a plurality of discrete level signals representative of said time dependent signal;
producing a different audible tone signal for each level of said discrete level signals;
producing audible sounds by driving a speaker to produce an audibly perceptible reference frame indicative of a predetermined time duration and driving said speaker with said audible tone signals such that said audible tone signals have the same time orientation with respect to each other as said discrete level signals have in said time dependant signal; and
providing said audible sounds to a human listener to enable said listener to distinguish the shape of said time dependent signal based on the position and time relation of said audible tone signals relative to said reference frame signal,
wherein said time dependent signal is an input signal to an oscilloscope, and including the step of controlling the operation of said digitizing means by a trigger circuit of said oscilloscope such that said method is synchronized with said oscilloscope.

10. A method comprising:
digitizing a time dependent signal to produce a plurality of discrete level signals representative of said time dependent signal;
producing a different audible tone signal for each level of said discrete level signals;
producing audible sounds by driving a speaker to produce an audibly perceptible reference frame indicative of a predetermined time duration and driving said speaker with said audible tone signals such that said audible tone signals have the same time orientation with respect to each other as said discrete level signals have in said time dependent signal; and
providing said audible sounds to a human listener to enable said listener to distinguish the shape of said time dependent signal based on the position and time relation of said audible tone signals relative to said reference frame signal,
wherein said digitizing step comprises writing information into a first memory at high speed and reading information out of said first memory at a low speed, writing the information read out of the first memory into a second memory at high speed and reading information out of said second memory at low speed.

11. A method for producing an audible image of a time dependent signal, comprising:
amplifying a received analog input signal and outputting said amplified input signal;
producing a digitized output signal representative of said amplified input signal;
writing portions of said digitized signal into memory locations at a first rate and reading data out of said memory locations at a second rate;
converting said data read out of said memory locations into an analog signal;
producing a frequency dependent signal having a frequency proportional to the amplitude of said analog converted signal;
producing an audible sound representation of said frequency dependent signal; and
producing an audibly perceptible reference frame signal; and
providing said audible sound and said audibly perceptible reference frame signal to a human listener to enable said listener to distinguish the shape of said time dependent signal based on the position and time relation of said audible tone signals relative to said reference frame signal.

* * * * *